United States Patent [19]

Pitteloud et al.

[11] Patent Number: 5,473,003
[45] Date of Patent: Dec. 5, 1995

[54] ALKANEDIPHENOLS

[75] Inventors: Rita Pitteloud, Praroman; Paul Dubs, Marly, both of Switzerland; Bernard Gilg, St. Louis-La-Chausee, France

[73] Assignee: Ciba-Geigy Corporation, Ardsley, N.Y.

[21] Appl. No.: 361,012

[22] Filed: Dec. 21, 1994

Related U.S. Application Data

[63] Continuation of Ser. No. 145,441, Oct. 28, 1993, abandoned.

[30] Foreign Application Priority Data

Nov. 5, 1992 [CH] Switzerland .............................. 3430/92

[51] Int. Cl.$^6$ .............................. C07C 39/12; C08K 5/34
[52] U.S. Cl. .......................... 524/291; 524/326; 524/334; 524/343; 524/344; 568/729
[58] Field of Search .................................. 524/334, 291, 524/326, 343, 344; 568/729

[56] References Cited

U.S. PATENT DOCUMENTS

| | | | |
|---|---|---|---|
| 2,321,620 | 6/1943 | Pratt ......................................... | 568/729 |
| 3,116,305 | 12/1963 | Morris et al. ............................ | 524/291 |
| 3,378,516 | 4/1968 | Tholstrup et al. ....................... | 524/343 |
| 3,711,554 | 1/1973 | Engelhardt et al. ..................... | 260/591 |
| 3,878,149 | 4/1975 | Fischer et al. .......................... | 524/291 |
| 3,952,072 | 4/1976 | Yonemitsu et al. . . | |
| 4,021,408 | 5/1977 | Horn et al. .............................. | 524/291 |
| 4,260,832 | 4/1981 | Parker et al. ............................ | 568/790 |
| 4,716,252 | 12/1987 | Wagner .................................... | 568/729 |

FOREIGN PATENT DOCUMENTS

| | | |
|---|---|---|
| 2009504 | 9/1971 | Germany . |
| 2454124 | 5/1975 | Germany . |

OTHER PUBLICATIONS

Thyagarajan et al., Chemistry & Industry (1967) 401 C. A. Registry No. 25598-19-0.
Plekhanova et al., Bull. Acad. Sci. USSR, Div. Chem. Sci. (Engl. Transl.) 22,819 (1973).
C.A. 76: 25934q.

*Primary Examiner*—Veronica P. Hoke
*Attorney, Agent, or Firm*—Michele A. Kovaleski

[57] ABSTRACT

Compositions comprising an organic material which is sensitive to thermal, oxidative and/or actinic degradation and at least one compound of the formula I

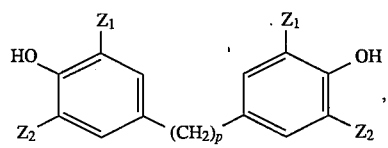

in which $Z_1$ and $Z_2$ independently of one another are $C_1$–$C_{18}$alkyl, $C_5$–$C_8$cycloalkyl, phenyl, phenyl-$C_1$–$C_4$alkyl or ($C_1$–$C_4$alkyl)phenyl and p is a number from 4 to 18, with the proviso that $Z_1$ and $Z_2$ are not simultaneously tertiary alkyl radicals. Some of the compounds of the formula I are novel.

The compounds of the formula I can also be employed as stabilizers as a mixture with compounds of the formula VI and/or of the formula VII

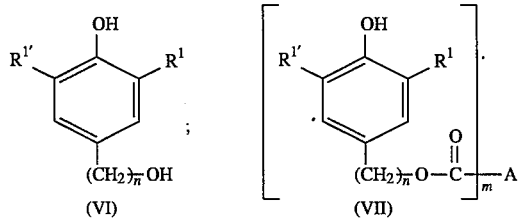

in which n and the radicals $R^1$, $R^{1\prime}$ and A are as defined in claims 14 and 15.

10 Claims, No Drawings

ALKANEDIPHENOLS

This is a continuation of application Ser. No. 08/145,441, filed on Oct. 28, 1993, now abandoned.

The present invention relates to novel α,ω-alkanediphenols, the organic materials stabilized with these compounds, if appropriate as a mixture with ω-hydroxyalkylphenols or esters thereof, against thermal, oxidative and actinic degradation, and to the use of the novel compounds as stabilizers.

Di-tert-butyl-substituted bisphenol compounds in which the phenol groups are linked via carboxyalkylene groups are known, inter alia, from U.S. Pat. No. 3,711,554. The compounds are used as stabilizers in polyolefins.

U.S. Pat. No. 4,260,832 describes a process for the alkylation of 2,6-di-tert-alkyl-substituted phenols with α,ω-alkanediols. Phenols which are substituted by OH-terminated alkane chains are prepared by this process. Corresponding bis(3',5'-di-tert-alkyl-4'-hydroxyphenyl)alkane compounds are obtained as by-products. Claisen rearrangement of 1,4-bis(2,6-dimethylphenoxy)-cis- and -trans-2-butenes is reported in Chemistry and Industry 1967, 401–2. 1,4-bis(3,5-dimethyl-4-hydroxyphenyl)butane is obtained by hydrogenation of the phenol formed. In Bull. Acad. Sci. USSR Div. Chem. Sci. (English translation) 22, (1973), 819–22, L. G. Plekhanova et at. describe the formation of quinoid derivatives of di-tert-butyl-substituted phenols in the context of studies on the reactions of 2,6-di-tert-butyl-cyclohexadienone-carbene. The compounds 1,4-di(4'-hydroxy-3',5'-di-tert-butylphenyl)butane and 1,8-di(4'-hydroxy-3',5'-di-tert-butylphenyl)octane are obtained by hydrogenation of the quinones. 1,4-Di(4'-hydroxy-3'-di-tert-butyl-5'-methylphenyl)butane is published in Chemical Abstracts under Registry Number 25598-19-0. Di-tert-butyl-substituted bisphenols, inter alia, are described as antioxidants in DE-A-2 009 504.

Some novel α,ω-alkanediphenols which have particularly good stabilizer properties have now been found.

The present invention therefore relates to compositions comprising an organic material which is sensitive to thermal, oxidative and/or actinic degradation and at least one compound of the formula I

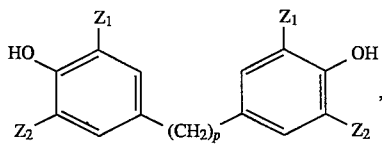

in which $Z_1$ and $Z_2$ independently of one another are $C_1$–$C_{18}$alkyl, $C_5$–$C_8$cycloalkyl, phenyl, phenyl-$C_1$–$C_4$alkyl or $C_7$–$C_{10}$alkylphenyl and p is a number from 4 to 18, with the proviso that $Z_1$ and $Z_2$ are not simultaneously tertiary alkyl radicals.

The invention likewise relates to novel compounds of the formula I, in which $Z_1$ and $Z_2$ independently of one another are $C_1$–$C_{18}$alkyl, $C_5$–$C_8$cycloalkyl, phenyl, phenyl-$C_1$–$C_4$alkyl or $C_7$–$C_{10}$alkylphenyl and p is a number from 4 to 18, with the proviso that if the two radicals $Z_1$ and $Z_2$ are $C_1$–$C_{18}$alkyl, one of the radicals is branched $C_1$–$C_{18}$alkyl, and with the proviso that the two radicals $Z_1$ and $Z_2$ are not simultaneously tertiary alkyl radicals, and with the proviso that the compound 1,4-bis(3'-tert-butyl-5'-methyl-4'-hydroxyphenyl)butane is not included.

$C_1$–$C_{18}$Alkyl $Z_1$ and $Z_2$ is a branched or unbranched radical. Branched $C_1$–$C_8$ alkyl is to be understood as meaning both radicals with secondary C atoms and those with tertiary C atoms. Examples of branched and unbranched $C_1$–$C_{18}$alkyl radicals are methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl, methyl and tert-butyl being particularly preferred.

$C_5$–$C_8$Cycloalkyl $Z_1$ and $Z_2$ are cyclopentyl, cyclohexyl, cycloheptyl or cyclooctyl, cyclopentyl and cyclohexyl being preferred.

Phenyl-$C_1$–$C_4$alkyl $Z_1$ and $Z_2$ are linear or branched $C_1$–$C_4$ alkyl substituted by phenyl, for example benzyl, phenethyl, 3-phenylpropyl, 4-phenylbutyl, α-methylbenzyl or α,α-dimethylbenzyl, preferably benzyl, α-methylbenzyl or α,α-dimethylbenzyl, in particular benzyl.

$C_7$–$C_{10}$Alkylphenyl $Z_1$ and $Z_2$ are a phenyl radical substituted by linear or branched $C_1$–$C_4$alkyl. The phenyl ring here can be mono- or polysubstituted, in particular mono- to trisubstituted, especially mono- or disubstituted, preferably monosubstituted. Examples of such radicals are tolyl, mesityl, xylyl, ethylphenyl, propylphenyl, diethylphenyl, ethylmethylphenyl or butylphenyl.

Examples of compounds of the formula I according to the invention and compounds of the formula I which are used in compositions according to the invention are:
1,4-bis(3'-tert-butyl-5'-methyl-4'-hydroxyphenyl)butane
1,5-bis(3'-tert-butyl-5'-methyl-4'-hydroxyphenyl)pentane
1,6-bis(3'-tert-butyl-5'-methyl-4'-hydroxyphenyl)hexane
1,7-bis(3'-tert-butyl-5'-methyl-4'-hydroxyphenyl)heptane
1,8-bis(3'-tert-butyl-5'-methyl-4'-hydroxyphenyl)octane
1,9-bis(3'-tert-butyl-5'-methyl-4'-hydroxyphenyl)nonane
1,10-bis(3'-tert-butyl-5'-methyl-4'-hydroxyphenyl)decane
1,11-bis(3'-tert-butyl-5'-methyl-4'-hydroxyphenyl)undecane
1,12-bis(3'-tert-butyl-5'-methyl-4'-hydroxyphenyl)dodecane
1,4-bis(3'-tert-butyl-5'-i-propyl-4'-hydroxyphenyl)butane
1,5-bis(3'-tert-butyl-5'-i-propyl-4'-hydroxyphenyl)pentane
1,6-bis(3'-tert-butyl-5'-i-propyl-4'-hydroxyphenyl)hexane
1,7-bis(3'-tert-butyl-5'-i-propyl-4'-hydroxyphenyl)heptane
1,8-bis(3'-tert-butyl-5'-i-propyl-4'-hydroxyphenyl)octane
1,9-bis(3'-tert-butyl-5'-i-propyl-4'-hydroxyphenyl)nonane
1,10-bis(3'-tert-butyl-5'-i-propyl-4'-hydroxyphenyl)decane
1,11-bis(3'-tert-butyl-5'-i-propyl-4'-hydroxyphenyl)undecane
1,12-bis(3'-tert-butyl-5'-i-propyl-4'-hydroxyphenyl)dodecane
1,4-bis(3'-tert-butyl-5'-cyclohexyl-4'-hydroxyphenyl)butane
1,5-bis(3'-tert-butyl-5'-cyclohexyl-4'-hydroxyphenyl)pentane
1,6-bis(3'-tert-butyl-5'-cyclohexyl-4'-hydroxyphenyl)hexane
1,7-bis(3'-tert-butyl-5'-cyclohexyl-4'-hydroxyphenyl)heptane
1,8-bis(3'-tert-butyl-5'-cyclohexyl-4'-hydroxyphenyl)octane
1,9-bis(3'-tert-butyl-5'-cyclohexyl-4'-hydroxyphenyl)nonane
1,10-bis(3'-tert-butyl-5'-cyclohexyl-4'-hydroxyphenyl)decane
1,11-bis(3'-tert-butyl-5'-cyclohexyl-4'-hydroxyphenyl)undecane 1,12-bis(3'-tert-butyl-5'-cyclohexyl-4'-hydroxyphenyl)dodecane
1,4-bis(3'-i-propyl-5'-methyl-4'-hydroxyphenyl)butane
1,5-bis(3'-i-propyl-5'-methyl-4'-hydroxyphenyl)pentane
1,6-bis(3'-i-propyl-5'-methyl-4'-hydroxyphenyl)hexane
1,7-bis(3'-i-propyl-5'-methyl-4'-hydroxyphenyl)heptane
1,8-bis(3'-i-propyl-5'-methyl-4'-hydroxyphenyl)octane
1,9-bis(3'-i-propyl-5'-methyl-4'-hydroxyphenyl)nonane
1,10-bis(3'-i-propyl-5'-methyl-4'-hydroxyphenyl)decane
1,11-bis(3'-i-propyl-5'-methyl-4'-hydroxyphenyl)undecane
1,12-bis(3'-i-propyl-5'-methyl-4'-hydroxyphenyl)dodecane
1,4-bis(3',5'-di-cyclohexyl-4'-hydroxyphenyl)butane
1,5-bis(3',5'-di-cyclohexyl-4'-hydroxyphenyl)pentane
1,6-bis(3',5'-di-cyclohexyl-4'-hydroxyphenyl)hexane
1,7-bis(3',5'-di-cyclohexyl-4'-hydroxyphenyl)heptane
1,8-bis(3',5'-di-cyclohexyl-4'-hydroxyphenyl)octane
1,9-bis(3',5'-di-cyclohexyl-4'-hydroxyphenyl)nonane
1,10-bis(3',5'-di-cyclohexyl-4'-hydroxyphenyl)decane
1,11-bis(3',5'-di-cyclohexyl-4'-hydroxyphenyl)undecane
1,12-bis(3',5'-di-cyclohexyl-4'-hydroxyphenyl)dodecane
1,4-bis(3',5'-diphenyl-4'-hydroxyphenyl)butane
1,5-bis(3',5'-diphenyl-4'-hydroxyphenyl)pentane
1,6-bis(3',5'-diphenyl-4'-hydroxyphenyl)hexane
1,7-bis(3',5'-diphenyl-4'-hydroxyphenyl)heptane
1,8-bis(3',5'-diphenyl-4'-hydroxyphenyl)octane
1,9-bis(3',5'-diphenyl-4'-hydroxyphenyl)nonane
1,10-bis(3',5'-diphenyl-4'-hydroxyphenyl)decane
1,11-bis(3',5'-diphenyl-4'-hydroxyphenyl)undecane
1,12-bis(3',5'-diphenyl-4'-hydroxyphenyl)dodecane
1,4-bis(3'-tert-amyl-5'-methyl-4'-hydroxyphenyl)butane
1,5-bis(3'-tert-amyl-5'-methyl-4'-hydroxyphenyl)pentane
1,6-bis(3'-tert-amyl-5'-methyl-4'-hydroxyphenyl)hexane
1,7-bis(3'-tert-amyl-5'-methyl-4'-hydroxyphenyl)heptane
1,8-bis(3'-tert-amyl-5'-methyl-4'-hydroxyphenyl)octane
1,9-bis(3'-tert-amyl-5'-methyl-4'-hydroxyphenyl)nonane
1,10-bis(3'-tert-amyl-5'-methyl-4'-hydroxyphenyl)decane
1,11-bis(3'-tert-amyl-5'-methyl-4'-hydroxyphenyl)undecane
1,12-bis(3'-tert-amyl-5'-methyl-4'-hydroxyphenyl)dodecane
1,4-bis(3'-cyclohexyl-5'-methyl-4'-hydroxyphenyl)butane
1,5-bis(3'-cyclohexyl-5'-methyl-4'-hydroxyphenyl)pentane
1,6-bis(3'-cyclohexyl-5'-methyl-4'-hydroxyphenyl)hexane
1,7-bis(3'-cyclohexyl-5'-methyl-4'-hydroxyphenyl)heptane
1,8-bis(3'-cyclohexyl-5'-methyl-4'-hydroxyphenyl)octane
1,9-bis(3'-cyclohexyl-5'-methyl-4'-hydroxyphenyl)nonane
1,10-bis(3'-cyclohexyl-5'-methyl-4'-hydroxyphenyl)decane
1,11-bis(3'-cyclohexyl-5'-methyl-4'-hydroxyphenyl)undecane
1,12-bis(3'-cyclohexyl-5'-methyl-4'-hydroxyphenyl)dodecane
1,4-bis(3'-methyl-5'-phenyl-4'-hydroxyphenyl)butane
1,5-bis(3'-methyl-5'-phenyl-4'-hydroxyphenyl)pentane
1,6-bis(3'-methyl-5'-phenyl-4'-hydroxyphenyl)hexane
1,7-bis(3'-methyl-5'-phenyl-4'-hydroxyphenyl)heptane
1,8-bis(3'-methyl-5'-phenyl-4'-hydroxyphenyl)octane
1,9-bis(3'-methyl-5'-phenyl-4'-hydroxyphenyl)nonane
1,10-bis(3'-methyl-5'-phenyl-4'-hydroxyphenyl)decane
1,11-bis(3'-methyl-5'-phenyl-4'-hydroxyphenyl)undecane
1,12-bis(3'-methyl-5'-phenyl-4'-hydroxyphenyl)dodecane
1,4-bis(3'-i-propyl-5'-phenyl-4'-hydroxyphenyl)butane
1,5-bis(3'-i-propyl-5'-phenyl-4'-hydroxyphenyl)pentane
1,6-bis(3'-i-propyl-5'-phenyl-4'-hydroxyphenyl)hexane
1,7-bis(3'-i-propyl-5'-phenyl-4'-hydroxyphenyl)heptane
1,8-bis(3'-i-propyl-5'-phenyl-4'-hydroxyphenyl)octane
1,9-bis(3'-i-propyl-5'-phenyl-4'-hydroxyphenyl)nonane
1,10-bis(3'-i-propyl-5'-phenyl-4'-hydroxyphenyl)decane
1,11-bis(3'-i-propyl-5'-phenyl-4'-hydroxyphenyl)undecane
1,12-bis(3'-i-propyl-5'-phenyl-4'-hydroxyphenyl)dodecane
1,4-bis(3'-sec-butyl-5'-tert-pentyl-4'-hydroxyphenyl)butane
1,5-bis(3'-sec-butyl-5'-tert-pentyl-4'-hydroxyphenyl)pentane
1,6-bis(3'-sec-butyl-5'-tert-pentyl-4'-hydroxyphenyl)hexane
1,7-bis(3'-sec-butyl-5'-tert-pentyl-4'-hydroxyphenyl)heptane
1,8-bis(3'-sec-butyl-5'-tert-pentyl-4'-hydroxyphenyl)octane
1,9-bis(3'-sec-butyl-5'-tert-pentyl-4'-hydroxyphenyl)nonane
1,10-bis(3'-sec-butyl-5'-tert-pentyl-4'-hydroxyphenyl)decane
1,11-bis(3'-sec-butyl-5'-tert-pentyl-4'-hydroxyphenyl)undecane
1,12-bis(3'-sec-butyl-5'-tert-pentyl-4'-hydroxyphenyl)dodecane Compounds of the formula I which are particularly preferably used are:
1,6-bis(3'-tert-butyl-5'-methyl-4'-hydroxyphenyl)hexane and
1,4-bis(3'-tert-butyl-5'-methyl-4'-hydroxyphenyl)butane.

Preferred compositions are those comprising compounds of the formula I,
in which
$Z_1$ and $Z_2$ independently of one another are $C_1$–$C_{18}$alkyl, $C_5$–$C_8$cycloalkyl, phenyl, benzyl, α-methylbenzyl or α,α-dimethylbenzyl and
p is a number from 4 to 12.

Other interesting compositions comprise compounds of the formula I,
in which
$Z_1$ and $Z_2$ independently of one another are $C_1$–$C_4$alkyl, $C_5$–$C_6$cycloalkyl, phenyl, benzyl, α-methylbenzyl or α,α-dimethylbenzyl.

Compositions which are of importance are those comprising compounds of the formula I,
in which
$Z_1$ and $Z_2$ independently of one another are methyl, tert-butyl, cyclohexyl, phenyl or α,α-dimethylbenzyl and
p is a number from 4 to 10;
in particular those,
in which
$Z_1$ is tert-butyl, cyclohexyl, phenyl or α,α-dimethylbenzyl and
$Z_2$ is methyl.

Compositions which are furthermore preferred are those comprising compounds of the formula I,
in which
one of the radicals $Z_1$ or $Z_2$ is tert-butyl.

Compositions which are of interest in particular are those comprising compounds of the formula I,
in which
$Z_1$ is tert-butyl and
$Z_2$ is methyl.

Preferred compounds of the formula I are those,
in which
p is a number from 4 to 12, in particular 4 to 10, for example 5 to 10, for example 6 to 8 or 8 to 10.

Compositions which are likewise prepared are those in which, in the compounds of the formula I, if the two radicals $Z_1$ and $Z_2$ are alkyl, one of the radicals is branched alkyl.

Various processes can be used for preparation of the compounds of the formula I.

The symbols $Z_1$, $Z_2$ and p in the formulae I–V given below are as defined above for formula I.

A) The bisphenols according to the invention can be prepared, for example, by a process analogous to that described in U.S. Pat. No. 4,260,832 by alkylation of phenols of the formula (II):

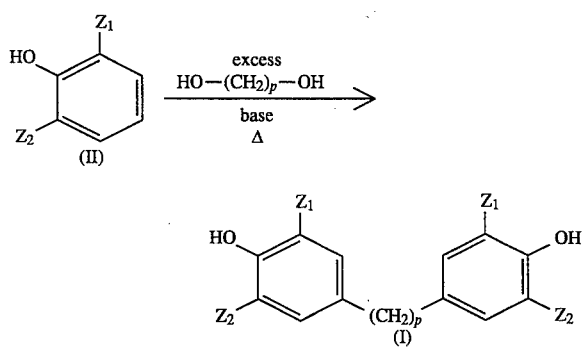

The process parameters for the preparation of the compounds according to the invention can be found in the US patent cited above. The bisphenols are advantageously isolated from the distillation residue after the ω-hydroxyphenylalkanols formed have been distilled off. This is effected, for example, by customary methods, such as crystallization, as described, for example, in Example 1 of the abovementioned patent specification, or chromatography.

B) The compounds of the formula I can also be prepared, for example, by Friedel-Crafts para-acylation of phenols (II) with his-acid chlorides with subsequent hydrogenation of the resulting bisketones (III).

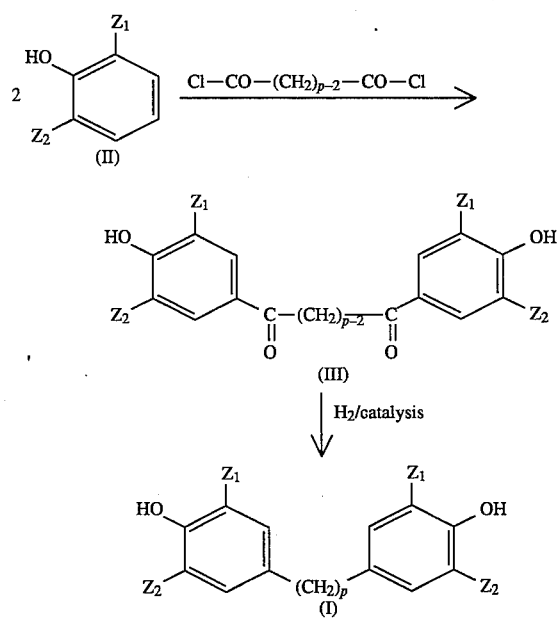

The acylation reaction can be carried out in a manner which is known per se, advantageously by adding one of the two educts to the second educt and mixing the two reaction partners, preferably with exclusion of oxygen. The reaction is advantageously carried out in the presence of a solvent, for example a chlorinated hydrocarbon, for example methylene chloride, or an aromatic hydrocarbon, for example toluene. Aluminium chloride is advantageously added as the catalyst for the acylation reaction. The temperature can be between the melting point and the boiling point of the reaction mixture, for example between −70° and 100° C., preferably between −65° and 0° C. The resulting product can likewise be purified by known methods, for example by washing with water/HCl, extraction with an organic solvent, crystallization and/or chromatography. Preferred solvents for the chromatographic purification step are hexane, ethyl acetate or mixtures thereof.

The hydrogenation is carried out by methods customary in the art, such as are described in numerous textbooks and standard works on organic chemistry, for example in Houben-Weyl, Methoden der Organischen Chemie (Methods of Organic Chemistry), Volume V/1a, 244 et seq., Georg Thieme Verlag, Stuttgart (1970). The keto compounds can thus be converted into the corresponding alkanes, for example, by catalytic hydrogenation, Clemmensen reduction with Zn(Hg)/hydrochloric acid or Wolff-Kishner reduction with hydrazine and subsequent reaction of the hydrazone with alkali.

Catalytic hydrogenation is particularly suitable. The hydrogenation reaction is advantageously carried out by stirring or shaking the compound to be hydrogenated with the catalyst in a suitable solvent. If the compound is liquid, the reaction can also be carried out without a solvent. The reaction is carried out in a hydrogen atmosphere in an apparatus in which the hydrogen uptake can be measured. An autoclave, for example, is advantageous. The catalysts used are, for example, platinum and palladium as the metal or on a charcoal support or nickel catalysts, in particular Raney nickel, but especially Pd/C. The hydrogenation conditions depend on the particular catalyst system used. Hydrogenation over platinum and palladium catalysts can be carried out, for example, under normal pressure or under slightly increased pressure, at temperatures of, for example, 20°–50° C. It is advantageous to carry out the reaction in an acid medium in order to increase the rate of reaction. For this, catalytic amounts of a mineral acid, for example sulfuric acid, are advantageously employed. Solvents which can be used for the hydrogenation are, for example, alcohols, such as methanol or ethanol, or aliphatic hydrocarbons, for example pentane or hexane, or glacial acetic-acid or ethyl acetate. After the catalyst has been filtered off, the compounds according to the invention are isolated by methods customary in the art, for example distillation, crystallization or chromatography.

C) Claisen/Cope rearrangement reactions of 1,4-di(2,6-di-substituted-phenoxy)-but-2-enes (IV) with subsequent hydrogenation of the resulting 1,4-bis(3',5'-di-substituted-6'-hydroxyphenyl)-but-2-enes (V) are also suitable, for example, as a further preparation process for compounds of the formula I where p=4.

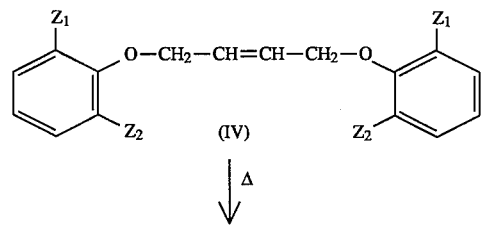

-continued

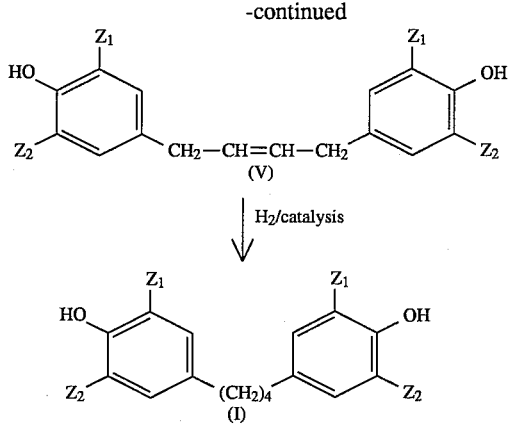

The rearrangement reactions are generally known to the expert and their mechanisms are described in numerous textbooks of organic chemistry (for example in H. J. Shine, Reaction Mechanisms in Organic Chemistry, Monograph 6, Elsevier Publishing Company, Amsterdam, London, New York, 1967, page 82 et seq. or in Houben-Weyl, Methoden der Organischen Chemie (Methods of Organic Chemistry), Volume VI/1c, Georg Thieme Verlag, Stuttgart, 1976). They are initiated by heating the compounds. Temperatures which are suitable for this depend on the particular compounds and are, for example, in the range of 160°–210° C. The reactions are advantageously carried out in high-boiling solvents, for example ethyldiglycol or N-diethylaniline. The compounds are isolated by customary methods, for example distillation, crystallization or chromatography.

Reduction of the phenylalkene to the corresponding phenylalkane is carried out by methods known to the expert, such as are described, for example, in numerous textbooks and standard works on organic chemistry, for example in Houben-Weyl, Methoden der Organischen Chemie (Methods of Organic Chemistry), Volume V/1a, Georg Thieme Verlag, Stuttgart (1970), 405 et seq.

Catalytic hydrogenation is particularly suitable. It is advantageously carried out as described under B).

The educts for the reactions described above are generally known and they are prepared by methods customary in the art. The his-ethers (IV) can be obtained, for example, by reaction of 1,4-dichlorobut-2-ene with 2 mol of the corresponding $Z_1,Z_2$-disubstituted phenol.

Mixtures of compounds of the formula I and those of the formula VI

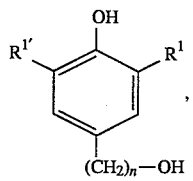

in which $R^1$ and $R^{1'}$ independently of one another are $C_1$–$C_{18}$alkyl, $C_5$–$C_8$cycloalkyl, phenyl, phenyl-$C_1$–$C_4$alkyl or $C_7$–$C_{10}$alkylphenyl and n is a number from 4 to 18, can also advantageously be employed as stabilizers. The invention therefore likewise relates to compositions comprising (a) an organic material which is sensitive to oxidative, thermal and/or actinic degradation, (b) a compound of the formula I as described further above and (c) a compound of the formula VI.

The invention furthermore relates to a composition comprising (a) an organic material which is sensitive to oxidative, thermal and/or actinic degradation, (b) a compound of the formula I as described further above and (c) a compound of the formula VII

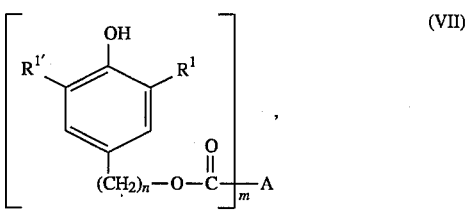

in which n is an integer in the range from 4 to 18 and m is an integer in the range from 1 to 4;

A, if m=1, is $C_1$–$C_{25}$alkyl, which is unsubstituted or substituted by $C_5$–$C_8$cycloalkyl; or $C_2$–$C_{25}$alkyl which is interrupted by $C_5$–$C_8$cycloalkyl or one or more of the groups —S—, —O— and/or —$NR^2$—; or A, if m=1, is $C_5$–$C_8$cycloalkyl, which is unsubstituted or substituted by $C_1$–$C_{12}$alkyl or $C_2$–$C_{12}$alkenyl; $C_6$–$C_8$cycloalkenyl, which is unsubstituted or substituted by $C_1$–$C_{12}$alkyl or $C_2$–$C_{12}$alkenyl; phenyl, which is unsubstituted or substituted by $C_1$–$C_{12}$alkyl or $C_2$–$C_{12}$alkenyl; naphthyl, which is unsubstituted or substituted by $C_1$–$C_{12}$alkyl or $C_2$–$C_{12}$alkenyl; biphenyl, which is unsubstituted or substituted by $C_1$–$C_{12}$alkyl or $C_2$–$C_{12}$alkenyl; or $C_2$–$C_{25}$alkenyl; $C_6$–$C_{10}$bicycloalkenyl; $C_7$–$C_{12}$phenylalkyl; $C_8$–$C_{12}$phenylalkenyl; $C_{11}$–$C_{16}$naphthylalkyl; $C_{12}$–$C_{16}$ naphthylalkenyl; $C_{13}$–$C_{18}$biphenylalkyl; $C_{14}$–$C_{18}$biphenylalkenyl; or a group of the formula

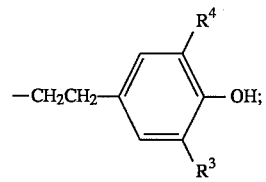

A, if m=2, is a direct bond; $C_1$–$C_{12}$alkylene; $C_2$–$C_{12}$alkenylene; $C_5$–$C_8$ cycloalkylene, which is unsubstituted or substituted by $C_1$–$C_{12}$alkyl or $C_2$–$C_{12}$alkenyl; $C_6$–$C_8$cycloalkenylene, which is unsubstituted or substituted by $C_1$–$C_{12}$alkyl or $C_2$–$C_{12}$alkenyl; $C_6$–$C_{10}$bicycloalkenylene; phenylene, naphthylene; a divalent heterocyclic radical from the group comprising furan, thiophene and pyrrole, which is saturated on the nitrogen atom by hydrogen or the substituent —$R^2$; or A, if m=2, is $C_2$–$C_{36}$alkylene which is interrupted by $C_5$–$C_8$cycloalkylene or phenylene or at least one of the groups —S—, —O— or —$NR^2$—;

A, if m=3, is $C_1$–$C_8$alkanetriyl; $C_2$–$C_8$alkenetriyl; benzenetriyl; naphthalenetriyl; a trivalent group of the formula

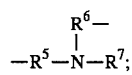

or $C_2$-$C_{18}$alkanetriyl which is interrupted by at least one of the groups —S—, —O— or —NR²—;

A, if m=4, is a benzene; naphthyl; tetrahydrofuryl or cyclohexyl radical having 4 free valencies;

$R^1$ and $R^{1'}$ independently of one another are $C_1$-$C_{18}$alkyl, $C_5$-$C_8$cycloalkyl, phenyl, phenyl-$C_1$-$C_4$alkyl or $C_7$-$C_{10}$alkylphenyl;

$R^2$ is H or $C_1$-$C_4$alkyl;

$R^3$ and $R^4$ independently of one another are $C_1$-$C_4$alkyl; and $R^5$, $R^6$ and $R^7$ independently of one another are $C_1$-$C_3$alkylene.

The invention therefore likewise relates to the use of mixtures of compounds of the formula I and of the formula VI, the use of mixtures of compounds of the formula I and of the formula VII and the use of mixtures of compounds of the formulae I, VI and VII for stabilizing organic material against oxidative, thermal or actinic degradation. This includes a process for stabilizing organic material against oxidative, thermal or actinic degradation, which comprises adding a mixture of compounds of the formula I and compounds of the formula VI and/or of the formula VII to this organic material.

$R^1$, $R^{1'}$ and n in the compounds of the formulae VI and VII are as preferred as for the radicals $Z_1$ and $Z_2$ and for the number p in the compounds of the formula I.

In the compounds of the formula VII, m is preferably 1 or 2, in particular 2.

Preferred compounds of the formula I in compositions comprising compounds of the formula VI and/or VII are the same as those in compositions without compounds of the formula VI or VII. By way of example, the instant compositions may contain 0 to 100 parts by weight of compounds of the formula VI and/or VII (component c) per 1 part of a compound of the formula I (component b). Preferred are compositions containing 5–95 parts by weight of component (c) per 95–5 parts of component (b); especially preferred are compositions containing ca. 30–70 parts by weight of component (c) per 70–30 parts of component (b).

A composition which is of particular industrial interest is one comprising (a) an organic material which is sensitive to oxidative, thermal and/or actinic degradation, (b) a compound of the formula I as defined further above and (c) a compound of the formula VII, in which A, if m=1, is $C_1$-$C_{25}$alkyl, which is unsubstituted or substituted by $C_5$-$C_8$cycloalkyl; or $C_2$-$C_{25}$alkyl, which is interrupted by $C_5$-$C_8$cycloalkyl or one or more of the groups —S—, —O— and/or —NR²—; or A, if m=1, is $C_5$-$C_8$cycloalkyl, which is unsubstituted or substituted by $C_1$-$C_{12}$alkyl; $C_6$-$C_8$cycloalkenyl, which is unsubstituted or substituted by $C_1$-$C_{12}$alkyl; phenyl, which is unsubstituted or substituted by $C_1$-$C_{12}$alkyl; or $C_2$-$C_{25}$alkenyl; $C_7$-$C_{12}$phenylalkyl; or a group of the formula

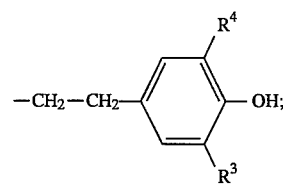

A, if m=2, is a direct bond; $C_1$-$C_{12}$alkylene; $C_2$-$C_{12}$alkenylene; $C_5$-$C_8$ cycloalkylene, which is unsubstituted or substituted by $C_1$-$C_{12}$alkyl; $C_6$-$C_8$cycloalkenylene, which is unsubstituted or substituted by $C_1$-$C_{12}$alkyl; phenylene; a divalent heterocyclic radical from the group comprising furan, thiophene and pyrrole, which is saturated on the nitrogen atom by hydrogen or the substituent —R²;

or A, if m=2, is $C_2$-$C_{18}$alkylene which is interrupted by $C_5$-$C_8$cycloalkylene or phenylene or at least one of the groups —S—, —O— or —NR²—;

and A, if m=3, is $C_1$-$C_8$alkanetriyl; $C_2$-$C_8$alkenetriyl; benzenetriyl; a trivalent group of the formula

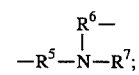

or $C_2$-$C_{18}$alkanetriyl, which is interrupted by at least one of the groups —S—, —O— or —NR²—; and A, if m=4, is a benzene or cyclohexyl radical having 4 free valencies.

Compounds of the formula VII which are particularly important as component (c) in these compositions are those, in which $R^{1'}$ is tert-butyl or cyclohexyl and $R^1$ is methyl, tert-butyl or cyclohexyl;

n is a number in the range from 4 to 8; and A, if m=1, is $C_6$-$C_{18}$alkyl or $C_2$-$C_{12}$ alkenyl;

A, if m=2, is a direct bond; $C_1$-$C_{12}$alkylene; phenylene;

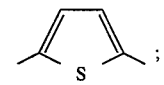

or $C_2$-$C_{36}$alkylene which is interrupted by 1 to 5 oxygen or sulfur atoms;

A, if m 3, is benzenetriyl or a trivalent group of the formula

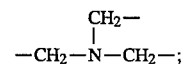

and

A, if m=4, is a benzene radical with 4 free valencies; in particular one of the compounds (a) to (l)

a) 6-(3-tert-butyl-4-hydroxy-5-methylphenyl)hexyl stearate;

b) 6-(3,5-di-tert-butyl-4-hydroxyphenyl)hexyl stearate;

c) bis[6-(3-tert-butyl-4-hydroxy-5-methylphenyl)hexyl] succinate;

d) bis[6-(3-tert-butyl-4-hydroxy-5-methylphenyl)hexyl]

adipate;

e) bis[6-(3-tert-butyl-4-hydroxy-5-methylphenyl)hexyl] suberate;

f) bis[6-(3-tert-butyl-4-hydroxy-5-methylphenyl)hexyl] isophthalate;

g) bis[6-(3,5-di-tert-butyl-4-hydroxyphenyl)hexyl] isophthalate;

h) tris[6-(3-tert-butyl-4-hydroxy-5-methylphenyl)hexyl] trimellitate;

j) tris[6-(3,5-di-tert-butyl-4-hydroxyphenyl)hexyl] trimellitate;

k) tris[6-(3-tert-butyl-4-hydroxy-5-methylphenyl)hexyl] trimesate; or l) tris[6-(3,5-di-tert-butyl-4-hydroxyphenyl)hexyl] trimesate.

The compounds of the formula VI and of the formula VII are known as stabilizers, and their preparation and use are described, for example, in GB-A-2 264 708.

The compounds of the formula I and mixtures of compounds of the formula I and compounds of the formulae VI or VII are suitable for stabilizing organic materials against thermal, oxidative and actinic degradation. Their outstanding action as antioxidants for stabilizing organic materials is to be pointed out in particular.

Examples of such materials are:

1. Polymers of mono- and diolefins, for example polypropylene, polyisobutylene, polybut-1-ene, poly-4-methylpent-1-ene, polyisoprene or polybutadiene, and polymers of cycloolefins, for example of cyclopentene or norbornene; and furthermore polyethylene (which can be crosslinked if appropriate), for example high-density polyethylene (HDPE), low-density polyethylene (LDPE), linear low-density polyethylene (LLDPE) and branched low-density polyethylene (BLDPE).

Polyolefins, i.e. polymers of monoolefins, such as are mentioned as examples in the above paragraph, in particular polyethylene and polypropylene, can be prepared by various processes, in particular by the following methods:

a) by free radicals (usually under a high pressure at a high temperature).

b) by means of a catalyst, the catalyst usually comprising one or more metals of group IVb, Vb, VIb or VIII. These metals usually have one or more ligands, such as oxides, halides, alcoholates, esters, ethers, amines, alkyls, alkenyls and/or aryls, which can be either π- or σ-coordinated. These metal complexes can be free or fixed to supports, for example to activated magnesium chloride, titanium(III) chloride, aluminium oxide or silicon oxide. These catalysts can be soluble or insoluble in the polymerization medium. The catalysts can be active as such in the polymerization, or other activators can be used, for example metal alkyls, metal hydrides, metal alkyl halides, metal alkyl oxides or metal alkyloxanes, the metals being elements of groups Ia, IIa and/or IIIa. The activators can be modified, for example, with further ester, ether, amine or silyl ether groups. These catalyst systems are usually called Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of various types of polyethylene (for example LDPE/HDPE).

3. Copolymers of mono- and diolefins with one another or with other vinyl monomers, for example, ethylene/propylene copolymers, linear low-density polyethylene (LLDPE) and mixtures thereof with low-density polyethylene (LDPE), propylene/1-butene copolymers, propylene/isobutylene copolymers, ethylene/1-butene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and copolymers thereof with carbon monoxide, or ethylene/acrylic acid copolymers and salts thereof (ionomers), as well as terpolymers of ethylene with propylene and a diene, such as hexadiene, dicyclopentadiene or ethylidenenorbornene; and furthermore mixtures of such copolymers with one another and with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers, LLDPE-ethylene/acrylic acid copolymers and alternatingly or randomly built-up polyalkylene-carbon monoxide copolymers and mixtures thereof with other polymers, for example polyamides.

4. Hydrocarbon resins (for example $C_5$–$C_9$), including hydrogenated modifications thereof (for example tackifying resins) and mixtures of polyalkylenes and starch.

5. Polystyrene, poly-(p-methylstyrene) and poly-(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate and methacrylate, styrene/maleic anhydride and styrene/acrylonitrile/methyl acrylate; toughened mixtures of styrene copolymers and another polymer, for example a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene.

7. Graft copolymers of styrene or α-methylstyrene, for example styrene on polybutadiene, styrene on polybutadiene/styrene or polybutadiene/acrylonitrile copolymers and styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under 6), such as are known, for example, as so-called ABS, MBS, ASA or AES polymers.

8. Halogen-containing polymers, for example polychloroprene, chlorinated rubber, chlorinated or chlorosulfonated polyethylene, copolymers of ethylene and chlorinated ethylene, epichlorohydrin homo- and copolymers, and in particular polymers of halogen-containing vinyl compounds, for example polyvinyl chloride, polyvinylidene chloride, polyvinyl fluoride and polyvinylidene fluoride; as well as copolymers thereof, such as vinyl chloride/vinylidene chloride, vinyl chloride/vinyl acetate or vinylidene chloride/vinyl acetate.

9. Polymers which are derived from α,β-unsaturated acids and derivatives thereof, such as polyacrylates and polymethacrylates, polymethyl methacrylates impact-modified with butyl acrylate, and polyacrylamides and polyacrylonitriles.

10. Copolymers of the monomers mentioned under 9) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers which are derived from unsaturated alcohols and amines, or acyl derivatives or acetals thereof, such as polyvinyl alcohol, polyvinyl acetate, stearate, benzoate and maleate, polyvinyl butyral, polyallyl phthalate and polyallylmelamine; and copolymers thereof with olefins mentioned under point 1.

12. Homopolymers and copolymers of cyclic ethers, such as polyalkylene glycols, polyethylene oxide, polypropylene oxide or copolymers thereof with bisglycidyl ethers.

13. Polyacetals, such as polyoxymethylene, and those polyoxymethylenes which contain comonomers, for example ethylene oxide; polyacetals modified with thermoplastic polyurethanes, acrylates or MBS.

14. Polyphenylene oxides and sulfides and mixtures thereof with polystyrene polymers or polyamides.

15. Polyurethanes which are derived from polyethers, polyesters and polybutadienes with terminal hydroxyl groups on the one hand and aliphatic or aromatic polyisocyanates on the other hand, and precursors thereof.

16. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12, 4/6 or 12/12, polyamide 11, polyamide 12 and aromatic polyamides starting from m-xylene, diamine and adipic acid; polyamides prepared from hexamethylenediamine and iso- and/or terephthalic acid and if appropriate an elastomer as a modifier, for example poly-2,4,4-trimethylhexamethylene-terephthalamide or poly-m-phenyleneisophthalamide. Block copolymers of the abovementioned polyamides with polyolefins, olefin copolymers, ionomers or chemically bonded or grafted elastomers; or with polyethers, for example with polyethylene glycol, polypropylene glycol or polytetramethylene glycol. Also, polyamides or copolyamides modified by EPDM or ABS; and polyamides condensed during processing ("RIM polyamide systems").

17. Polyureas, polyimides and polyamide-imides and polybenzimidazoles.

18. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoate and block polyether-esters which are derived from polyethers with hydroxyl end groups; and furthermore polyesters modified with polycarbonates or MBS.

19. Polycarbonates and polyester-carbonates.

20. Polysulfones, polyether-sulfones and polyether-ketones.

21. Crosslinked polymers which are derived from aldehydes on the one hand and phenols, urea and melamine on the other hand, such as phenol/formaldehyde, urea/formaldehyde and melamine/formaldehyde resins.

22. Drying and non-drying alkyd resins.

23. Unsaturated polyester resins which are derived from copolyesters of saturated and unsaturated dicarboxylic acids with polyhydric alcohols, as well as vinyl compounds as crosslinking agents, and also halogen-containing, poorly combustible modifications thereof.

24. Crosslinkable acrylic resins which are derived from substituted acrylic acid esters, for example from epoxyacrylates, urethane-acrylates or polyester-acrylates.

25. Alkyd resins, polyester resins and acrylate resins which are crosslinked with melamine resins, urea resins, polyisocyanates or epoxy resins.

26. Crosslinked epoxy resins which are derived from polyepoxides, for example from bisglycidyl ethers or from cycloaliphatic diepoxides.

27. Naturally occurring polymers, such as cellulose, natural rubber, gelatin and derivatives thereof which are chemically modified in a polymer-homologous manner, such as cellulose acetates, propionates and butyrates, and the cellulose ethers, such as methylcellulose; as well as colophony resins and derivatives.

28. Mixtures (polyblends) of the abovementioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic substances which are pure monomeric compounds or mixtures of such, for example mineral oils, animal or vegetable fats, oils and waxes, or oils, waxes and fats based on synthetic esters (for example phthalates, adipates, phosphates or trimellitates), as well as mixtures of synthetic esters with mineral oils in any weight ratios, such as are used, for example, as spinning preparations, and aqueous emulsions thereof.

30. Aqueous emulsions of naturally occurring or synthetic rubbers, for example natural rubber latex or latices of carboxylated styrene/butadiene copolymers.

The invention also relates to the use of compounds of the formula I for stabilizing organic material against oxidative, thermal or actinic degradation, and to a process for stabilizing organic material against thermal, oxidative and/or actinic degradation, which comprises adding at least one compound of the formula I to this material.

The use of compounds of the formula I as antioxidants in synthetic organic polymers is of particular interest.

Preferred organic materials are polymers, for example synthetic polymers, in particular thermoplastic polymers. Particularly preferred organic materials are polyolefins and styrene copolymers, for example those mentioned above under points 1 to 3 and under points 5 and 6, in particular polyethylene and polypropylene, as well as ABS and styrene/butadiene copolymers. The invention therefore preferably relates to compositions in which the organic material is a synthetic organic polymer or a mixture of such polymers, in particular a polyolefin or a styrene copolymer.

The compounds of the formula I or the mixtures of compounds of the formula I and those of the formula VI or VII are in general added to the material to be stabilized in amounts of 0.01 to 10%, preferably 0.01 to 5%, in particular 0.01 to 2%, based on the total weight of the material to be stabilized. The use of the compounds according to the invention in amounts of 0.01 to 0.5%, in particular 0.05 to 0.3%, is particularly preferred.

In addition to the compounds of the formulae I, VI and/or VII, the compositions according to the invention can additionally comprise conventional additives, for example those mentioned below.

1. Antioxidants 1.1. Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol and 2,6-didocecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate and bis(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol) and 4,4'-bis(2,6-dimethyl-4-hydroxyphenyl) disulfide.

1.5. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane and 1,1,5,5-tetra-(5-tert-butyl-4-hydroxy-2-methylphenyl)pentane.

1.6. O-, N- and S-Benzyl compounds, for example 3,5,3',5'-tetra-tert-butyl-4,4'-dihydroxydibenzyl ether, octadecyl 4-hydroxy-3,5-dimethylbenzyl mercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl) sulfide and isooctyl 3,5 -di-tert-butyl-4-hydroxybenzylmercaptoacetate.

1.7. Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methylbenzyl)malonate, didodecylmercaptoethyl 2,2-bis(3,5-di-tert-butyl-4-hydroxybenzyl)malonate and di-[4-(1,1,3,3-tetramethylbutyl)phenyl] 2,2-bis(3,5-di-tert-butyl-4-hydroxybenzyl)malonate.

1.8. Hydroxybenzyl-aromatics, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene and 2,4,6-tris(3,5-di-tert-butyl-4-hydroxybenzyl)phenol.

1.9. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine and 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate and the Ca salt of 3,5-di-tert-butyl-4-hydroxybenzylphosphonic acid monoethyl ester.

1.11. Acylaminophenols, for example 4-hydroxylauric acid anilide, 4-hydroxystearic acid anilide and octyl N-(3,5-di-tert-butyl-4-hydroxyphenyl)carbamate.

1.12. Esters of β-(3,5-di-tert-butyl-4-hydroxyphenyl)propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

1.13. Esters of β-(5-tert-butyl-4-hydroxy-3-methylphenyl)propionic acids with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

1.14. Esters of β-(3,5-dicyclohexyl-4-hydroxyphenyl)propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

1.15. Esters of 3,5-di-tert-butyl-4-hydroxyphenylacetic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

1.16. Amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'- bis(3,5-di-tert-butyl-4-hydroxyphenylpropionyl)trimethylenediamine and N,N'-bis(3,5-di-tert-butyl-4-hydroxyphenylpropionyl)hydrazine.

2. UV Absorbers and Light Stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl )phenyl )benzotriazole, 2-(3',5'-di-tert-butyl- 2'-hydroxyphenyl)-5-chlorbenzotriazole, 2-(3'-tert-butyl-2'-hydroxy-5'-methylphenyl)- 5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2' -hydroxyphenyl)benzotriazole, 2-(3',5'-bis(α,α-dimethylbenzyl)-2'-hydroxyphenyl)benzotriazole, a mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylenebis[ 4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl] benzotriazole with polyethyleneglycol 300; and [R—CH$_2$CH$_2$—COO(CH$_2$)$_3$—]$_2$, where R=3'-tert-butyl-4'-hydroxy-5'-2 H-benzotriazol-2-ylphenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy-derivates.

2.3. Esters of unsubstituted or substituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-ten-butyl-4-hydroxybenzoate, octadecyl 3,5-di-tert-butyl-4-hydroxybenzoate and 2-methyl-4,6-di-tert-butylphenyl 3,5-di-tert-butyl-4-hydroxybenzoate.

2.4. Acrylates, for example ethyl or isooctyl α-cyano-β,β-diphenylacrylate, methyl α-carbomethoxycinnamate, methyl and ethyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, if appropriate with additional ligands, such as n-butylamine, triethanolamine or N-cyclohexyldiethanolamine, nickel dibutyldithio carbamate, nickel salts of 4-hydroxy-3,5-di-tert-butylbenzylphosphonic acid monoalkyl esters, such as of the methyl or ethyl ester, nickel complexes of ketoximes, such as of 2-hydroxy-4-methylphenyl undecyl ketoxime and nickel complexes of 1-phenyl- 4-lauroyl-5-hydroxypyrazole, if appropriate with additional ligands.

2.6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, n-butyl-3,5-di-tert-butyl-4-hydroxybenzylmalonic acid bis(1,2,2,6,6-pentamethylpiperidyl) ester, the condensation product of 1-hydroxyethyl-2,2,6,6-tetramethyl-4-hydroxypiperidine and succinic acid, the condensation product of N,N'-bis(2,2,6,6-tetramethyl- 4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)-bis( 3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)- 2-n-butyl-2-(2-hydroxy-3,5-di-tert-butylbenzyl)malonate, 3-n-octyl-7,7,9,9-tetramethyl- 1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the condensation product of N,N'-bis(2,2,6,6-tetramethyl-4-piperidyl)hexamethylenediamine and 4-morpholino-2,6-dichloro-1,3,5-triazine, the condensation product of 2-chloro- 4,6-di-(4-n-butylamino-2,2,6,6-tetramethylpiperidyl)-1,3,5-triazine and 1,2-bis(3'-aminopropylamino)ethane, the condensation product of 2-chloro-4,6-di-(4-n-butylamino- 1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl- 1-(2,2,6,6-tetramethyl-4-piperidyl)pyrrolidine-2,5-dione and 3-dodecyl-1-(1,2,2,6,6-pentamethyl- 4-piperidyl)pyrrolidine-2,5-dione.

2.7. Oxalic acid diamides, for example 4,4'-dioctyloxyoxanilide, 2,2'-dioctyloxy-5,5' -di-tert-butyloxanilide, 2,2'-di-dodecyloxy-5,5'-di-tert-butyloxanilide, 2-ethoxy-2'-ethyloxanilide, N,N'-bis(3-dimethylaminopropyl)oxalamide, 2-ethoxy- 5-tert-butyl-2'-ethyloxanilide and a mixture thereof with 2-ethoxy-2'-ethyl-5,4'-di-tert-butyloxanilide, and mixtures of o- and p-methoxy- and of o- and p-ethoxy-di-substituted oxanilides.

2.8. 2-(2-Hydroxyphenyl)-1,3,5-triazines, for example 2,4,6-tris(2-hydroxy-4-octyloxyphenyl)- 1,3,5-triazine, 2-(2-hydroxy-4-octyloxyphenyl)-4,6-bis(2,4-dimethylphenyl)- 1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl] -4,6-bis(2,4-dimethylphenyl)-1,3,5-triazine and 2-[2-hydroxy-4-(2-hydroxy- 3-octyloxypropyloxy)phenyl]-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic acid dihydrazide, oxanilide, isophthalic acid dihydrazide, sebacic acid bisphenylhydrazide, N,N'-diacetyl adipic acid dihydrazide, N,N'-bissalicyloyloxalic acid dihydrazide and N,N'-bissalicyloyl-thiopropionic acid dihydrazide.

4. Phosphites and phosphonites, for example triphenyl phosphite, diphenyl alkyl phosphites, phenyl dialkyl phosphites, tris(nonylphenyl) phosphite; trilauryl phosphite, trioctadecyl phosphite, distearyl pentaerythrityl diphosphite, tris(2,4-di-tert-butylphenyl) phosphite, diisodecyl pentaerythrityl diphosphite, bis(2,4-di-ten-butylphenyl) pentaerythrityl diphosphite, bis(2,6-di-tert-butyl-4-methylphenyl) pentaerythrityl diphosphite, bisisodecyloxy pentaerythrityl diphosphite, bis(2,4-di-tert-butyl-6-methylphenyl) pentaerythrityl diphosphite, bis(2,4,6-tri-tert-butylphenyl) pentaerythrityl diphosphite, tristearyl sorbityl triphosphite, tetrakis(2,4-di-tert-butylphenyl) 4,4'-biphenylene diphosphonite, 6-isooctyloxy-2,4,8,10-tetra-tert-butyl-12H-dibenz[d,g]- 1,3,2-dioxaphosphocine, 6-fluoro-2,4, 8,10-tetra-tert-butyl-12-methyl-dibenz[d,g]-1,3,2-dioxaphosphocine, bis(2,4-di-tert-butyl-6-methylphenyl) methyl phosphite, bis(2,4-di-tert-butyl- 6-methylphenyl) ethyl phosphite.

5. Peroxide-destroying compounds, for example esters of β-thiodipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythrityl tetrakis(β-dodecylmercapto)propionate.

6. Polyamide stabilizers, for example copper salts in combination with iodides and/or phosphorus compounds and salts of divalent manganese.

7. Basic costabilizers, for example melamine, polyvinylpyrrolidone, dicyandiamide, triallyl cyanurate, urea derivates, hydrazine derivates, amines, polyamides, polyurethanes and alkali metal and alkaline earth metal salts of higher fatty acids, for example calcium stearate, zinc stearate, magnesium behenate, magnesium stearate, sodium ricinoleate, potassium palmitate, antimony pyrocatecholate or tin pyrocatecholate.

8. Nucleating agents, for example 4-tert-butylbenzoic acid, adipic acid and diphenylacetic acid.

9. Fillers and reinforcing agents, for example calcium carbonate, silicates, glass fibres, talc, kaolin, mica, barium sulfate, metal oxides and hydroxides, carbon black and graphite.

10. Other additives, for example plasticizers, lubricants, emulsifiers, pigments, fluorescent whiteners, flameproofing agents, antistatics and blowing agents.

11. Benzofuranones or indolinones, for example those described in U.S. Pat. No. 4,325,863, U.S. Pat. No. 4,338, 244 or U.S. Pat. No. 5,175,312, or 3-[4-(2-acetoxyethoxy)phenyl]-5,7 -di-ten-butyl-benzofuran- 2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxylphenyl)benzofuran-2-one], 5,7 -di-tert-butyl- 3-(4-ethoxyphenyl)benzofuran-2-one, 3-(4-acetoxy-3,5-dimethylphenyl)-5,7-di-tert-butylbenzofuran- 2-one, 3-(3,5-dimethyl-4-pivaloyloxyphenyl)-5,7-di-tert-butylbenzofuran- 2-one.

The conventional additives are added, for example, in concentrations of 0.01 to 10%, based on the total weight of the material to be stabilized.

The compound of the formula I and if appropriate other additives are usually incorporated into the organic material by known methods. The incorporation into the materials can be carried out, for example, by mixing the compounds of the formula I and if appropriate other additives in or applying them by the methods customary in the art. If the materials are polymers, in particular synthetic polymers, the incorporation can be carried out before or during shaping, or by application of the dissolved or dispersed compounds to the polymer, if appropriate with subsequent evaporation of the solvent. In the case of elastomers, these can also be stabilized as latices. Another possibility for incorporation of the compounds of the formula I into polymers comprises addition thereof before, during or immediately after the polymerization of the corresponding monomers or before crosslinking. The compounds of the formula I can be added here as such or else in encapsulated form (for example in waxes, oils or polymers). In the case of addition before or during the polymerization, the compounds of the formula I can also act as regulators for the chain length of the polymers (chain stoppers).

The compounds of the formula I can also be added to the materials to be stabilized in the form of a masterbatch which comprises these compounds, for example, in a concentration of 2.5 to 25% by weight.

The materials stabilized in this way can be used in widely varying forms, for example as films, fibres, tapes, moulding compositions or profiles, or as binders for varnishes, adhesives or putties.

The compositions according to the invention comprising compounds of the formula I (component b) and compounds of the formula VI or of the formula VII (component c) can likewise be prepared by the methods described above. Preferably, however, a mixture of components (b) and (c) is first prepared and is then incorporated as described above into the organic material to be stabilized. A mixture which can be employed according to the invention of compounds of the formula I and of the formula VI can advantageously be obtained directly by means of preparation process (A) described above and in U.S. Pat. No. 4,260,832, the excess alkanediol advantageously being removed and the mixture being further purified, if appropriate, before incorporation of the mixture.

The compounds of the formula VI which the mixture comprises, in addition to the compounds of the formula I, can advantageously be converted into esters of the formula VII by esterification or transesterification with organic carboxylic acids of the formula VIII

or derivatives of such carboxylic acids. This is advantageously effected after removal of the excess alkanediol; further purification steps are in general not necessary. The reaction can take place under the reaction conditions described in GB-A-2 264 708, using the derivatives of carboxylic acid VIII described therein. The mixture of compounds of the formulae I and VII which acts as a stabilizer can be obtained directly in this manner.

The following examples illustrate the invention in more detail. Parts and percentages are by weight, unless stated otherwise, as is the case in the rest of the description and in the patent claims. The abbreviations used in the examples have the following meanings:

NMR: nuclear magnetic resonance

HPLC: high pressure liquid chromatography

YI: yellowness index according to ASTM D 1925-70

DLTDP: dilauryl thiodipropionate

SBR: styrene/butadiene copolymer

EXAMPLE 1

Preparation of
1,6-bis(3'-tert-butyl-5'-methyl,4'-hydroxyphenyl)hexane (Preparation process A)

164.7 g (1 mol) of 2-tert-butyl-6-methylphenol are heated at 100° C. with 596.7 g (5.05 mol) of 1,6-hexanediol under nitrogen in a 1.5 l sulfonating flask with a water separator. After addition of 36.6 g (0.66 mol) of potassium hydroxide, the reaction mixture is kept at 240° C. for 11 hours. 43 ml of water are separated off. The reaction mixture is then cooled to 50° C. and 280 ml of 2N hydrochloric acid are added. The phases are separated and the aqueous phase is extracted with 200 ml of toluene. The combined organic phases are concentrated on a rotary evaporator and the oily residue is distilled in vacuo. 167 g of 6-(3'-tert-butyl-4'-hydroxy-5'-methylphenyl)hexanol are distilled off in this manner. Chromatography of the distillation residue (silica gel) gives 40 g (10% of theory) of the title product of melting point 47°–48° C.

Elemental analysis:

| Calculated: | C: 81.90% | Found: | C: 81.90% |
|---|---|---|---|
| | H: 10.31% | | H: 10.40% |

Typical signals in the $^1$H-NMR spectrum (300 MHz/ CDCl$_3$): Ar—$\underline{CH_2}$—(CH$_2$)$_4$—$\underline{CH_2}$—Ar δ=2.48 ppm, triplet, J=7.56 Hz.

EXAMPLE 2

Preparation of 1,5-bis(3'-tert-butyl-5'-methyl-4'-hydroxyphenyl)pentane (Preparation process B)

1) Friedel-Crafts acylation 27 g (200 mmol) of aluminium chloride, 6.5 ml (50 mmol) of glutaric acid chloride and 250 ml of methylene chloride are initially introduced into a 500 ml three-necked round-bottomed flask. The suspension is cooled to −60° C. and a solution of 18 g (110 mmol) of 2-tert-butyl-6-methylphenol in 30 ml of methylene chloride is added dropwise in the course of about 30–40 minutes. The hydrochloric acid gas which evolves is collected in water. The reaction mixture is stirred at −50° C. for 30 minutes and is then poured onto ice. After addition of 20 ml of concentrated hydrochloric acid, the mixture is stirred for about 10 minutes. The phases are separated and the organic phase is dried over sodium sulfate and freed from the solvent on a rotary evaporator. The 20 g of crude product thus obtained are purified by column chromatography (SiO$_2$, toluene/ethyl acetate 19:1). 12 g (56% of theory) of 1,5-di(3'-tert-butyl-5'-methyl-4'-hydroxyphenyl)-1,5-pentanedione of melting point 156°–158° C. result. The vibration band of the CO groups in the infra-red spectrum appears at 1663.7 cm$^{-1}$.

2) Catalytic hydrogenation 8.17 g (19 mmol) of 1,5-di(3'-tert-butyl-5'-methyl-4'-hydroxyphenyl)-1,5-pentanedione in 80 ml of ethyl acetate and 3–5 drops of concentrated sulfuric acid are hydrogenated over 1.6 g of Pd/C (5%) at room temperature under atmospheric pressure. After 12 hours, the uptake of hydrogen has ended. The catalyst is filtered over Celite and the resulting colourless solution is concentrated on a rotary evaporator. Chromatography of the liquid residue (SiO$_2$, hexane/ethyl acetate 19:1) gives 5.13 g (67% of theory) of 1,5-bis(3'-tert-butyl-5'-methyl-4'-hydroxyphenyl)pentane as a viscous oil.

Elemental analysis:

| Calculated: | C: 81.77% | Found: | C: 81.99% |
|---|---|---|---|
| | H: 10.17% | | H: 10.32% |

Typical signals in the $^1$H-NMR spectrum (300 MHz/ CDCl$_3$):Ar—$\underline{CH_2}$—(CH$_2$)$_3$—$\underline{CH}_2$—Ar δ=2.49 ppm, triplet, J=7.6 Hz.

EXAMPLE 3

Preparation of 1,10-bis(3'-ten-butyl-5'-methyl-4'-hydroxyphenyl)decane (Preparation process B)

1) Friedel-Crafts acylation 18 g (110 mmol) of 2-tert-butyl-6-methylphenol are reacted with 10.7 g (50 mmol) of decanedioic acid chloride in the presence of 27.5 g (200 mmol) of aluminium chloride by the method described in Example 2 to give the corresponding 1,10-di(3'-tert-butyl-5'-methyl-4'-hydroxyphenyl)-1,10-decanedione. 19.2 g (78% of theory) of the product of melting point 165°–168° C. are obtained. The vibration band of the CO groups in the infra-red spectrum appears at 1660. cm$^{-1}$.

2) Hydrogenation 7.2 g (13 mmol) of the 1,10-diketone are hydrogenated at room temperature under normal pressure for 9 hours by the method described in Example 2. 3.14 g (57% of theory) of 1,10-bis(3'-tert-butyl-5'-methyl-4'-hydroxyphenyl)decane of melting point 96°–98° C. are obtained.

Elemental analysis:

| Calculated: | C: 82.85% | Found: | C: 82.74% |
|---|---|---|---|
| | H: 11.34% | | H: 11.76% |

Typical signals in the $^1$H-NMR spectrum (300 MHz/ CDCl$_3$): Ar—$\underline{CH_2}$—(CH$_2$)$_8$—$\underline{CH}_2$—Ar δ=2.50 ppm, triplet, J=7.5 Hz.

EXAMPLE 4

Preparation of 1,4.-bis(3'-tert-butyl-5'-methyl-4-hydroxyphenyl)butane (Preparation process C)

1st stage: Preparation of 1,4-di(2'-tert-butyl-6'-methylphenoxy)but-2-ene

A mixture of 32 g (200 mmol) of 2-tert-butyl-6-methylphenol, 10.5 ml (100 mmol) of trans-1,4-dichlorobut-2-ene, 41.4 g (300 mmol) of potassium carbonate and 250 ml of dimethylformamide is stirred at 90° C. in a 750 ml sulfonating flask for 4 hours. After the reaction mixture has been cooled to room temperature, it is filtered over Celite, the filtrate is poured onto saturated aqueous ammonium chloride solution and the mixture is extracted with ethyl acetate. The organic phase is dried with sodium sulfate and, after the sodium sulfate has been filtered off, the filtrate is concentrated on a rotary evaporator. Chromatography (SiO$_2$, hexane) of the resulting brown oil (36 g) gives 18 g (47% of theory) of the desired bis-ether.

Elemental analysis:

| Calculated: | C: 82.06% | Found: | C: 81.90% |
|---|---|---|---|
| | H: 9.54% | | H: 9.67% |

2nd stage: Preparation of 1,4-bis(3'-tert-butyl-5'-methyl-4'-hydroxyphenyl)but-2-ene A solution of 25.6 g (67 mmol) of the ether described above in 170 ml of ethylene diglycol is stirred at 195° C. for 4 hours. The solvent is distilled off and the residue is chromatographed (SiO$_2$, hexane/ethyl acetate 40:1 ). 8.6 g (34% of theory) of 1,4-bis(3'-tert-butyl-5'-methyl-4'-hydroxyphenyl)but-2-ene with a melting range of 99°–106° C. results.

| Elemental analysis: | |
|---|---|
| Calculated: C: 82.06% | Found: C: 82.30% |
| H: 9.54% | H: 9.76% |

3rd stage: Preparation of 1,4-bis(3'-tert-butyl-5'-methyl-4'-hydroxyphenyl)butane 8.55 g (22.5 mmol) of 1,4-bis(3'-tert-butyl-5'-methyl-4'-hydroxyphenyl)but-2-ene in 100 ml of ethyl acetate are hydrogenated over 1 g of Pd/C (5%) at room temperature under atmospheric pressure. After 30 minutes, the uptake of hydrogen has ended. The reaction mixture is filtered over Celite and the resulting filtrate is concentrated. Crystallization of the crude product from acetonitrile gives 6.6 g (77% of theory) of 1,4-bis(3'-tert-butyl-5'-methyl-4'-hydroxyphenyl)butane of melting point 106°–107° C.

| Elemental analysis: | |
|---|---|
| Calculated: C: 81.62% | Found: C: 81.59% |
| H: 10.01% | H: 10.50% |

Typical signals in the $^1$H-NMR spectrum (300 MHz/CDCl$_3$): Ar—$\underline{CH_2}$—(CH$_2$)$_2$—$\underline{CH_2}$—Ar δ=2.52 ppm, triplet, J=7 Hz.

EXAMPLE 5

Preparation of 1,6-bis(3',5'-dicyclohexyl-4'-hydroxyphenyl)hexane (Preparation process A)

25 g (8% of theory) of the title product of melting point 162°–167° C. are obtained, in addition to 6-(3',5'-dicyclohexyl-4'-hydroxyphenyl)hexanol from 258 g (1 mol) of 2,6-dicyclohexylphenol and 590 g (5 mol) of 1,6-hexanediol by the method described in Example 1.

| Elemental analysis: | |
|---|---|
| Calculated: C: 84.22% | Found: C: 83.49% |
| H: 10.43% | H: 10.58% |

Typical signals in the $^1$H-NMR spectrum (300 MHz/CDCl$_3$): Ar—$\underline{CH_2}$—(CH$_2$)$_4$—$\underline{CH_2}$—Ar δ=2.51 ppm, triplet, J=7.48 Hz.

EXAMPLE 6

Preparation of a mixture of α,ω-alkanediphenol and hydroxyphenylalkanol ester

1) α,ω-Alkanediphenol and hydroxyphenylalkanol (preparation process A)

The procedure according to Example 1 is followed until the oily crude product is obtained. This is now freed from 28 g of unreacted 2-tert-butyl-6-methylphenol by means of vacuum distillation (114°–135° C., 2000 Pa). According to HPLC, the residue (about 240 g) contains 70% of 6-(3'-tert-butyl-4'-hydroxy-5'-methylphenyl)hexanol and 20% of 1,6-bis(3'-tert-butyl-5'-methyl-4'-hydroxyphenyl)hexane.

2) Esterification 11.1 g of the residue described under (1) (comprising 30 mmol of 6-(3'-tert-butyl-4'-hydroxy-5'-methylphenyl)hexanol), 3.66 g (21 mmol) of dimethyl adipate and 240 mg of dibutyltin oxide are introduced into a round-bottomed flask with a distillation attachment. The mixture is heated to 190° C., methanol being distilled off. The mixture is kept at 190° C. for a further 5 hours. After cooling to 20°–25° C., the crude mixture is purified by chromatography (SiO$_2$; hexane/ethyl acetate 19/1). 7.8 g (50% of theory) of pale yellow powder (melting range 55°–93° C.) which comprises 29% of hexanediphenol (A) and 62% of diester (B) (HPLC) are obtained.

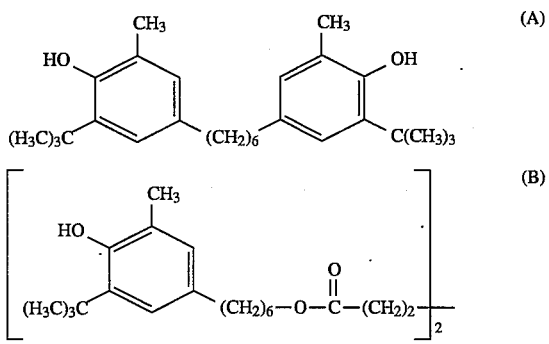

EXAMPLE 7

Stabilizing of acrylonitrile/butadiene/styrene terpolymer (ABS)

The stabilizers shown in Table 1 are dissolved in 40 ml of a mixture of hexane and isopropanol. The solution is added to a dispersion of 100 g of ABS in 600 ml of water, while stirring vigorously, after which the solution is absorbed completely by the ABS in the course of about 1 minute. The polymer powder comprising the stabilizers is then filtered off and dried at 40° C. in vacuo for 40 hours.

The subsequent processing steps are also carried out with a sample without stabilizers, for comparison purposes.

2% of titanium dioxide, as a pigment, and 1% of ethylenebis-stearic acid amide, as a lubricant, are added to the dry powder. The mixture is then compounded on a twin-roll mill at 180° C. in the course of 4 minutes.

A sheet 0.8 mm thick is pressed out of the rolled hide at 175° C., and test specimens of 45×17 mm$^2$ are stamped out of the sheet. Testing of the activity of the stabilizers added is carried out by heat ageing in a circulating air oven at 180° C. The development of colour after a test period of 45 minutes serves as the criterion. The colour intensity is determined in accordance with ASTM D 1925-70 (Yellowness Index). The test results are summarized in Table 1. Higher figures mean a more intensive yellow colouration. The experiments show that the yellow colouration is suppressed effectively by the compounds according to the invention.

TABLE 1

| Stabilizers | YI after 45 minutes oven ageing at 180° C. |
|---|---|
| none | 78 |
| 0.5% of DLTDP* | 75 |
| 0.25% of the compound from Example 1 + 0.5% of DLTDP | 28 |
| 0.25% of the compound from Example 2 + 0.5% of DLTDP | 28 |
| 0.25% of the compound from Example 3 + 0.5% of DLTDP | 29 |
| 0.25% of the compound from Example 4 + 0.5% of DLTDP | 28 |
| 0.25% of the compound mixture from Example 6 + 0.5% of DLTDP | 30 |

*DLTDP = Dilauryl thiodipropionate

EXAMPLE 8

Stabilizing of X-SBR (carboxylated SBR latex)

In each case 0.25 part by weight of the stabilizers according to the invention listed in Table 2 are dissolved in a little methanol and the solution is stirred into 100 parts by weight of X-SBR latex (type XZ 99466.00 from the manufacturer DOW Chemical Corp.). A precisely defined amount of latex is then introduced into Petri dishes and drying in a drying cabinet at 80° C. Transparent films with a layer thickness of about 0.2 mm are obtained. For comparison purposes, a sample is prepared without stabilizers.

Testing of the activity of the stabilizers added is carried out by heat ageing in a circulating air oven at 120° C. The discolouration of the samples is determined in accordance with ASTM D 1925-70 (Yellowness Index [YI]) after the intervals of time shown in Table 2. The test results are summarized in Table 2. Higher numbers mean a more intensive yellow colouration. The experiments show that the yellow colouration is suppressed effectively by the compounds according to the invention.

TABLE 2

YI after the ageing time stated (in hours) at 120° C.

| Stabilizer | Yellowness Index after an ageing time of | | | |
|---|---|---|---|---|
| | 0 hour | 6 hours | 21 hours | 28 hours |
| None | 7 | 38 | 147 | * |
| 0.25% of compound No. 1 | 5 | 13 | 37 | 45 |

*not measurable (sample black)

We claim:

1. A composition comprising (a) a styrene copolymer which is sensitive to thermal, oxidative or actinic degradation and (b) an effective stabilizing amount of a compound of the formula I

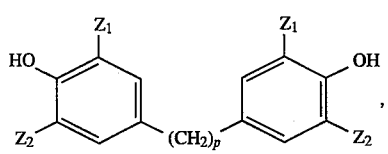

in which $Z_1$ and $Z_2$ independently of one another are $C_1$–$C_{18}$alkyl, $C_5$–$C_8$cycloalkyl, phenyl, phenyl-$C_1$–$C_4$alkyl or $C_7$–$C_{10}$ alkylphenyl and p is a number from 4 to 18, with the proviso that $Z_1$ and $Z_2$ are not simultaneously tertiary alkyl radicals.

2. A composition according to claim 1, in which, in formula I, $Z_1$ and $Z_2$ independently of one another are $C_1$–$C_{18}$alkyl, $C_5$–$C_8$cycloalkyl, phenyl, benzyl, α-methylbenzyl or α,α-dimethylbenzyl, and p is a number from 4 to 12.

3. A composition according to claim 1, in which, in formula I, $Z_1$ and $Z_2$ independently of one another are $C_1$–$C_4$alkyl, $C_5$–$C_6$cycloalkyl, phenyl, benzyl, α-methylbenzyl or α,α-dimethylbenzyl.

4. A composition according to claim 1, in which, in formula I, $Z_1$ and $Z_2$ independently of one another are methyl, tert-butyl, cyclohexyl, phenyl or α,α-dimethylbenzyl and p is a number from 4 to 10.

5. A composition according to claim 1, in which, in formula I, one of the radicals $Z_1$ or $Z_2$ is tert-butyl.

6. A composition according to claim 5, in which, in formula I, $Z_1$ is tert-butyl and $Z_2$ is methyl.

7. A composition according to claim 6, in which, in formula I, p is a number from 4 to 10.

8. A process for stabilizing a styrene copolymer against thermal, oxidative or actinic degradation, which comprises adding an effective stabilizing amount of a compound of the formula I according to claim 1 to this material.

9. A compound of the formula I

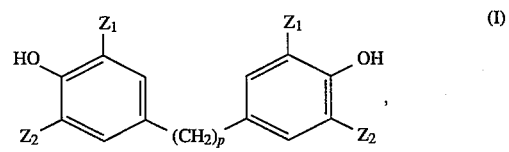

in which $Z_1$ and $Z_2$ independently of one another are $C_1$–$C_{18}$alkyl, $C_5$–$C_8$cycloalkyl, phenyl, phenyl-$C_1$–$C_4$alkyl or $C_7$–$C_{10}$alkylphenyl and p is a number from 4 to 10, with the proviso that if the two radicals $Z_1$ and $Z_2$ are $C_1$–$C_{18}$alkyl, one of the radicals is branched $C_1$–$C_{18}$alkyl, and with the proviso that the two radicals $Z_1$ and $Z_2$ are not simultaneously tertiary alkyl radicals, and with the proviso that the compound 1,4-bis(3'-tert-butyl-5'-methyl-4'-hydroxyphenyl)butane is not included.

10. A composition comprising (a) a styrene copolymer which is sensitive to oxidative, thermal or actinic degradation, (b) an effective stabilizing amount of a compound of the formula I according to claim 1 and (c) an effective stabilizing amount of a compound of the formula VII

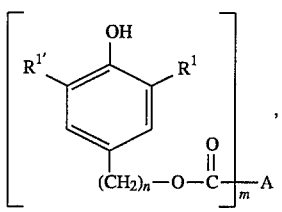

in which n is an integer in the range from 4 to 18 and m is an integer in the range from 1 to 4;

A, if m=1, is $C_1$–$C_{25}$alkyl, which is unsubstituted or substituted by $C_5$–$C_8$cycloalkyl; or $C_2$–$C_{25}$alkyl which is interrupted by $C_5$–$C_8$cycloalkyl or a group selected from the bivalent radicals —S—, —O— and —NR$^2$—; or A, if m=1, is $C_5$–$C_8$cycloalkyl, which is unsubstituted or substituted by $C_1$–$C_{12}$alkyl or $C_2$–$C_{12}$alkenyl; $C_6$–$C_8$cycloalkenyl, which is unsubstituted or substituted by $C_1$–$C_{12}$alkyl or $C_2$–$C_{12}$alkenyl; phenyl, which is unsubstituted or substituted by $C_1$–$C_{12}$alkyl or $C_2$–$C_{12}$alkenyl; naphthyl, which is unsubstituted or substituted by $C_1$–$C_{12}$alkyl or $C_2$–$C_{12}$alkenyl; biphenyl, which is unsubstituted or substituted by $C_1$–$C_{12}$alkyl or $C_2$–$C_{12}$alkenyl; or $C_2$–$C_{25}$alkenyl; $C_6$–$C_{10}$bicycloalkenyl; $C_7$–$C_{12}$phenylalkyl; $C_8$–$C_{12}$phenylalkenyl; $C_{11}$–$C_{16}$naphthylalkyl; $C_{12}$–$C_{16}$naphthylalkenyl; $C_{13}$–$C_{18}$biphenylalkyl; $C_{14}$–$C_{18}$biphenylalkenyl; or a group of the formula

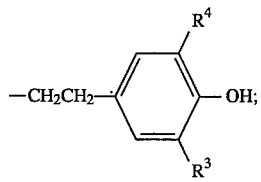

A, if m=2, is a direct bond; $C_1$–$C_{12}$alkylene; $C_2$–$C_{12}$alkenylene; $C_5$–$C_8$ cycloalkylene, which is unsubstituted or substituted by $C_1C_{12}$alkyl or $C_2$–$C_{12}$alkenyl; $C_6$–$C_8$cycloalkenylene, which is unsubstituted or substituted by $C_1$–$C_{12}$alkyl or $C_2$–$C_{12}$alkenyl; $C_6$–$C_{10}$bicycloalkenylene; phenylene, naphthylene; a divalent heterocyclic radical from the group comprising furan, thiophene and pyrrole, which is saturated on the nitrogen atom by hydrogen or the substituent —R$^2$; or A, if m=2, is $C_2$–$C_{36}$alkylene which is interrupted by $C_5$–$C_8$cycloalkylene or phenylene or —S—, —O— or —NR$^2$—;

A, if m=3, is $C_1$–$C_8$alkanetriyl; $C_2$–$C_8$alkenetriyl; benzenetriyl; naphthalenetriyl; a trivalent group of the formula

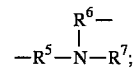

or $C_2$–$C_{18}$alkanetriyl, which is interrupted by a group —S—, —O— or —NR$^2$—;

A, if m=4, is a benzene, naphthyl, tetrahydrofuryl or cyclohexyl radical having 4 free valencies;

$R^1$ and $R^{1'}$ independently of one another are $C_1$–$C_{18}$alkyl, $C_5$–$C_8$cycloalkyl, phenyl, phenyl-$C_1$–$C_4$alkyl or $C_7$–$C_{10}$alkylphenyl;

$R^2$ is H or $C_1$–$C_4$alkyl;

$R^3$ and $R^4$ independently of one another are $C_1$–$C_4$alkyl; and $R^5$, $R^6$ and $R^7$ independently of one another are $C_1$–$C_3$alkylene.

\* \* \* \* \*